United States Patent
Branan et al.

(10) Patent No.: US 12,322,204 B2
(45) Date of Patent: Jun. 3, 2025

(54) MULTISPECTRAL OPTICAL FINGER SYSTEM FOR PHYSIOLOGICAL MEASUREMENTS

(71) Applicant: THE TEXAS A&M UNIVERSITY SYSTEM, College Station, TX (US)

(72) Inventors: Kimberly Branan, College Station, TX (US); Gerard L. Cote, College Station, TX (US); Justin Mcmurray, College Station, TX (US)

(73) Assignee: THE TEXAS A&M UNIVERSITY SYSTEM, College Station, TX (US)

( * ) Notice: Subject to any disclaimer, the term of this patent is extended or adjusted under 35 U.S.C. 154(b) by 0 days.

(21) Appl. No.: 18/418,887

(22) Filed: Jan. 22, 2024

(65) Prior Publication Data
US 2024/0249553 A1 Jul. 25, 2024

Related U.S. Application Data

(60) Provisional application No. 63/440,197, filed on Jan. 20, 2023.

(51) Int. Cl.
*G06V 40/145* (2022.01)
*G06F 3/01* (2006.01)

(52) U.S. Cl.
CPC ............ *G06V 40/145* (2022.01); *G06F 3/014* (2013.01)

(58) Field of Classification Search
CPC ... G06V 40/145; G06F 3/014; A61B 5/14552; A61B 5/681; A61B 5/6826
See application file for complete search history.

(56) References Cited

U.S. PATENT DOCUMENTS

| | | | |
|---|---|---|---|
| 8,145,288 B2 * | 3/2012 | Baker, Jr. ............. | A61B 5/6826 600/326 |
| 10,413,182 B2 * | 9/2019 | Flitsch ............... | G06Q 30/0261 |
| 11,191,466 B1 * | 12/2021 | Heneghan ................ | A61B 5/01 |
| 11,399,749 B2 * | 8/2022 | Lee ...................... | A61B 5/6801 |
| 2008/0033412 A1 * | 2/2008 | Whelan .................... | A61N 5/01 607/90 |
| 2011/0007035 A1 * | 1/2011 | Shai ...................... | G06F 3/0304 345/179 |
| 2011/0210931 A1 * | 9/2011 | Shai ..................... | G06F 3/03547 345/173 |
| 2014/0365009 A1 * | 12/2014 | Wettels ................ | B25J 19/023 700/258 |
| 2016/0077582 A1 * | 3/2016 | Song ..................... | G06F 3/0488 345/173 |
| 2017/0035308 A1 * | 2/2017 | Gulati ................ | G01N 21/4795 |
| 2017/0049417 A1 * | 2/2017 | Liu ........................ | A61B 8/445 |
| 2020/0000441 A1 * | 1/2020 | Lafon ................ | A61B 5/02438 |
| 2020/0253479 A1 * | 8/2020 | Nurmikko .......... | A61B 5/14553 |

(Continued)

*Primary Examiner* — William Lu
(74) *Attorney, Agent, or Firm* — Barnes & Thornburg LLP

(57) ABSTRACT

Wearable optical devices, methods and systems for obtain dynamic and static physiological parameters from a subject are disclosed. Example devices can be worn around an appendage, such as a finger, and utilize PPG sensors to obtain signals from the appendage. The PPG sensors are positioned to acquire signals suitable to reconstruct an image of the inner appendage using, for example, diffuse optical tomography, to provide additional information. The devices, methods, and systems can obtain dynamic and static physiological parameters and accurate images in real-time.

22 Claims, 11 Drawing Sheets

(56) References Cited

U.S. PATENT DOCUMENTS

| | | | |
|---|---|---|---|
| 2021/0038083 A1* | 2/2021 | Islam | G01J 3/28 |
| 2021/0097520 A1* | 4/2021 | Adari | G06F 21/6209 |
| 2021/0204815 A1* | 7/2021 | Koskela | A61B 5/681 |
| 2021/0337885 A1* | 11/2021 | Connor | A41C 3/0064 |
| 2021/0407684 A1* | 12/2021 | Pho | A61B 5/7475 |
| 2022/0233142 A1* | 7/2022 | Hasan | A61B 5/681 |
| 2022/0287649 A1* | 9/2022 | Leabman | A61B 5/02438 |
| 2022/0334639 A1* | 10/2022 | Sanchez | B60K 35/80 |
| 2022/0409060 A1* | 12/2022 | Connor | A61B 5/6804 |
| 2023/0036474 A1* | 2/2023 | Kaede | G06F 3/017 |
| 2024/0099617 A1* | 3/2024 | Sell | G01N 33/025 |
| 2024/0180428 A1* | 6/2024 | Islam | A61B 5/14546 |

* cited by examiner

MULTISPECTRAL OPTICAL FINGER SYSTEM FOR PHYSIOLOGICAL MEASUREMENTS

CROSS-REFERENCE TO RELATED APPLICATIONS

This application claims priority to and the benefit of U.S. Provisional Application Ser. No. 63/440,197, entitled "MULTISPECTRAL OPTICAL FINGER SYSTEM FOR PHYSIOLOGICAL MEASUREMENTS" and filed Jan. 20, 2023, the contents of which are incorporated by reference herein in its entirety.

GOVERNMENT RIGHTS

This invention was made with government support under Award Number 1648451 provided by NSF. The government has certain rights in this invention.

FIELD

The present disclosure relates to devices, methods, and systems for obtaining biosignals from a patient and reconstructing an image to identify the source of the signal and, specifically, to finger-worn devices that can acquire time-domain-based signals and tomographic-based reconstructions from these signals.

BACKGROUND

Physiological measurements are an essential hallmark of the healthcare industry. Without the ability to measure dynamic parameters, static parameters, and other physiological parameters in patients, it would be impossible to treat the subjects for diseases and ailments effectively. Recent advances in wearable technology allow monitoring of these physiological measurements outside the clinic, which allows patients to continue with their daily lives while constantly monitoring their health and well-being. The technology also gives physicians the ability to monitor physiological parameters in a patient remotely. One widely used technique for measuring physiological parameters is photoplethysmography (PPG). PPG is the measure of blood volume changes within an area of tissue being probed by a light source, typically a light-emitting diode (LED). PPG signals can be acquired by transmission mode, where the light sources and detector are on the opposite sides of the subject, or reflective mode, where the light sources and detector are on the same side of the subject.

In clinical applications, PPG signals are acquired from the tip of the finger using transmission mode to measure blood oxygenation and heart rate. Health and fitness trackers often utilize a wrist-worn device to obtain biosignals since such devices can be comfortably worn on the wrist during everyday activities. However, major arteries within the wrist area are deeper within the tissue relative to the finger. Moreover, since the wrist area is denser than the finger and light can only travel a few millimeters, wrist devices are designed to measure PPG signals in reflectance mode. Wearable devices can be positioned at the base of the finger as a ring, but unlike the fingertip, the lower phalanx has a more complicated anatomy with a significant amount of opaque tissue and bone. A challenge to the use of PPG is the arbitrary nature in which signals are acquired. A PPG signal is a combination of all the blood volume changes within an area of tissue, including superficial blood vessels and the major artery in question. To determine the blood volume change of the major artery, the blood volume change of the remaining tissues can be estimated and the results are offset by the estimated amount, which can lead to inaccurate results.

Diffuse Optical Tomography (DOT) is an optical imaging technique typically used for soft tissue. DOT can be used to isolate major arteries by quantifying total hemoglobin concentration along with oxyhemoglobin and deoxyhemoglobin to identify blood oxygenation levels. This technique can also identify areas of higher concentrations of water and lipids along with measuring blood volume change within a tissue region. Traditional DOT systems use significant power-consuming components, making the system unsuitable for wearable devices, and typically utilize lasers, fiber optic cables, and CCD cameras for detection, which creates high power, relatively high cost, and a large equipment requirements typically placed on a benchtop. DOT systems have been designed for the finger, in particular for investigating the progress of rheumatoid arthritis within the finger joints, but not for measuring real-time hemodynamics such as blood volume changes. An additional issue with diffuse optics is the inability to resolve the correct image and display accurate changes in hemodynamics. Dependent on the DOT technique, real-time images have not yet been developed due to the complexity of the image reconstruction algorithms.

Accordingly, there is a need for improved wearable devices, methods, and systems to obtain PPG signals as well as an accurate reconstructed image to isolate the signal from the artery and superficial vessels.

SUMMARY

Examples of the present disclosure include ring devices that utilize multi-wavelength photoplethysmography (PPG) sensors to obtain biosignals. For instance, due to the complexity and the ability to measure signals in both transmission and reflective modes, example ring devices of the present disclosure can overcome the limitations of known arm, wrist, chest and other finger-based PPG sensors. Furthermore, examples of the present disclosure include devices with dual sensing modes for both dynamic and static measurements along with the ability to measure signals from superficial blood vessels in addition to signals coming from the major arteries. Dynamic measurements can include but are not limited to blood volume changes, hemoglobin concentration changes (e.g. blood oxygenation), blood velocity, pulse wave velocity, and blood flow through the finger. Other dynamic measurements that can be derived from these metrics include but are not limited to heart rate, heart rate variability, respiration rate, blood pressure, arterial and venous blood oxygenation, stroke volume, and cardiac output. Static signals measured via the ring device can include but are not limited to bone and tendon locations, the concentration of fat, and the concentration of water.

Photoplethysmography (PPG) is the measure of blood volume changes within an area of tissue being probed by a light source, typically a light-emitting diode (LED). In operation, light travels through tissue and is absorbed, reflected, and mostly scattered before it is detected with a photodiode (PD). The resulting signal acquired by the photodiode is a cyclical signal oscillating with the cardiac cycle. An oscillating component of the signal, known as the AC component, originates from the pulsatile arterial blood. The AC component is summed with a large offset related to non-pulsatile arterial blood, venous blood, and other bone and tissue matter, known as the quasi-DC component.

Examples of the present disclosure utilizes diffuse optical tomography (DOT) systems to create an image of the internal finger and accurately identify the location of major arteries, bones, and tendons. With this information, signals from different areas of interest can be isolated.

A known challenge with diffuse optical imaging such as DOT is the inability to solve the forward or inverse problems to resolve the correct image and display accurate changes in hemodynamics. The forward problem is summarized as solving the diffuse equation to determine the rate of photons traveling through the tissue, given the optical and physiological properties at each point in the tissue. In contrast, the inverse problem uses measured rates of the photons traveling through the tissue to determine the optical and physiological properties at each point in the tissue. Reconstructing an image by solving the inverse problem is ill-posed, computationally expensive, and undetermined. This is due to the iterative nature of the linear and non-linear approaches for solving the forward and inverse models. Further, without accurate scattering and absorption coefficients, resolving and reconstructing an image displaying accurate blood volume changes is difficult.

Example systems of the present disclosure include a neural network implementing a forward model to solve the inverse problem. The addition of deep learning provides a computationally inexpensive, real-time solution to the inverse problem to construct an accurate image displaying changes in blood volume and hemoglobin concentrations. The PPG and DOT systems of the present disclosure can accurately identify major vessel location, which can, in turn, provide relative blood volume, and hemoglobin concentration changes along with measurement of physiological parameters such as heart rate, heart rate variability, respiration rate, and blood oxygenation. Examples of the present disclosure include the ability to measure all of these signals simultaneously to provide additional physiological parameters such as blood velocity, flow rate, pulse wave velocity, cardiac output, blood pressure, and other physiological metrics dependent on hemodynamics. Examples of the present disclosure can reconstruct images and provide physiological parameters to a user in real-time or close to real-time.

In one aspect, a wearable optical device is disclosed that can include a ring configured to surround an appendage, the ring including an outer surface and an inner surface facing the appendage. The device further includes a plurality of light sources disposed circumferentially about the inner surface and configured to direct light towards the appendage and a plurality of detectors disposed circumferentially about the inner surface, each detector configured to receive light from the appendage, the light being reflected from and/or transmitted through the appendage from at least one of the plurality of light sources. In some embodiments, a circuit board is disposed within the ring and operatively connected to each of the plurality of light sources and the plurality of detectors and the plurality of light sources and the plurality of detectors are configured to operate together to generate data suitable for conducting diffuse optical tomography on the appendage.

In certain embodiments, the device defines an open position, where the plurality of light sources and the plurality of detectors are disposed proximal to the inner surface, and a closed position, where the plurality of light sources and the plurality of detectors are contacting the appendage, the device being operable to move between the open position and the closed position.

In certain embodiments, the device further includes a carrier disposed within a recess formed in the inner surface of the ring, the carrier configured to couple the plurality of light sources and the plurality of detectors to the ring.

In certain embodiments, each of the plurality of light sources comprises a contact surface configured to contact the appendage and each of the plurality of detectors comprises a contact surface configured to contact the appendage. The plurality of light sources and the plurality of detectors can be arranged in pairs and each light source and detector of each pair can be disposed within a common housing. In some embodiments, the device further includes a plurality of biasing mechanisms each configured to bias a respective one of the common housings towards the appendage. Each common housing can be configured to move along a respective radial axis and prevented from rotating relative to the carrier.

In certain embodiments, the device includes a plurality of pressure sensors, each pressure sensor configured to measure pressure of the appendage against the contact surfaces of at least one of a respective one of the plurality of light sources and the plurality of detectors. The device can further include a plurality of position sensors, each position sensor configured to measure radial deflection of at least one of the plurality of light sources and the plurality of detectors by the appendage.

In certain embodiments, the plurality of light sources includes eight light sources disposed at equal intervals about the circumference of the inner surface, and the plurality of detectors includes eight detectors disposed at equal intervals about the circumference of the inner surface. In some embodiments, each light source of the plurality of light sources includes an array of light-emitting diodes, each array comprising a plurality of individual light-emitting diodes each configured to emit light in a different wavelength.

In certain embodiments, the device includes a microcontroller configured to cause the emission of light from each of the plurality of light sources and receive the data from each of the plurality of detectors. The device can further include a wireless transmitter configured to transmit the data. In some embodiments, the device includes at least one of a skin temperature sensor, an ambient temperature sensor, or a sensor configured to measure movement of the device.

In another aspect, a method of obtaining a signal from a subject is disclosed that can include providing a wearable optical device disposed around an appendage, the device comprising a plurality of light sources and a plurality of detectors disposed circumferentially around the appendage. The method can further include emitting light from one of the plurality of light sources individually, receiving signals from each of the plurality of detectors, repeating the emitting and receiving for each of the plurality of light sources, and generating data from the received signals, the data being suitable for conducting 2D or 3D diffuse optical tomography on the appendage.

In certain embodiments, the method can further include moving the plurality of light sources and the plurality of detectors towards the appendage until they contact the appendage. The signals can be received from two or more photodiodes at a time.

In some embodiments, the method can further include receiving by a processor, the data from the device of disposed around the appendage, reconstructing an image of the appendage using the data and diffuse optical tomography techniques, isolating a biosignal from an internal structure within the appendage, and providing physiological information based on the biosignal.

In certain embodiments, the biosignal includes a dynamic signal and the physiological information includes at least one of: blood volume changes, blood oxygenation, blood velocity, pulse wave velocity, or blood flow. In some embodiments, the biosignal includes a static signal and the physiological information includes at least one of: bone location, tendon location, fat concentration, or water concentration.

In certain embodiments, the image is reconstructed and the physiological information is provided in real-time. The internal structure can be a main artery of the appendage. In some embodiments, the data is processed using a deep learning model to obtain the reconstructed image of the appendage.

DETAILED DESCRIPTION

Figure 1A:
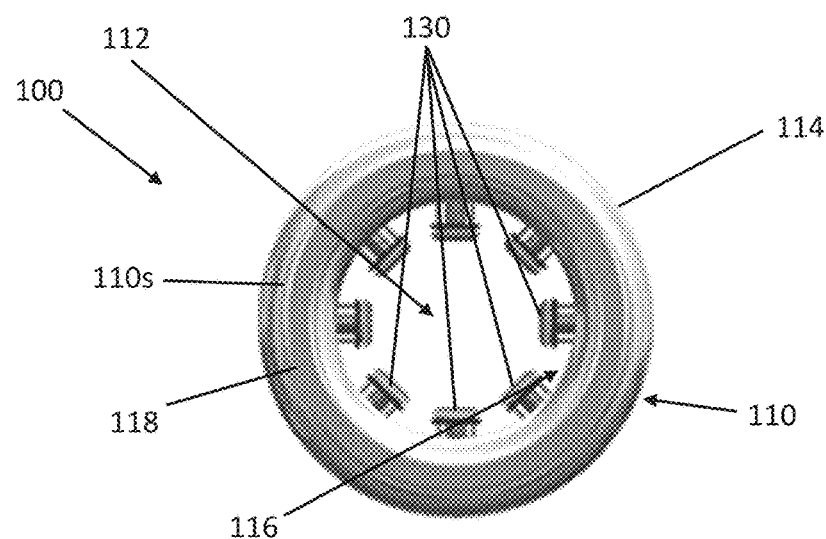
FIG. 1A is a front view of one exemplary embodiment of a wearable optical device.

Certain exemplary embodiments will now be described to provide an overall understanding of the principles of the structure, function, manufacture, and use of the devices, systems, and methods disclosed herein. One or more examples of these embodiments are illustrated in the accompanying drawings. Those skilled in the art will understand that the devices, systems, components related to or otherwise part of such devices, systems, and methods specifically described herein and illustrated in the accompanying drawings are non-limiting embodiments and that the scope of the present disclosure is defined solely by the claims. The features illustrated or described in connection with one embodiment may be combined with the features of other embodiments. Such modifications and variations are intended to be included within the scope of the present disclosure. Some of the embodiments provided for herein may be schematic drawings, including possibly some that are not labeled as such but will be understood by a person skilled in the art to be schematic in nature. They may not be to scale or may be somewhat crude renderings of the disclosed components. A person skilled in the art will understand how to implement these teachings and incorporate them into work systems, methods, and components related to each of the same, provided for herein.

To the extent the present disclosure includes various terms for components and/or processes of the disclosed devices, systems, methods, and the like, one skilled in the art, in view of the claims, present disclosure, and knowledge of the skilled person, will understand such terms are merely examples of such components and/or processes, and other components, designs, processes, and/or actions are possible. In the present disclosure, like-numbered and like-lettered components of various embodiments generally have similar features when those components are of a similar nature and/or serve a similar purpose. To the extent terms such as front, back, top, bottom, proximal, distal, etc. are used to describe a location of various components of the various disclosures, such usage is by no means limiting, and is often used for convenience when describing various possible configurations.

Articles "a" and "an" are used herein to refer to one or to more than one (i.e., at least one) of the grammatical object of the article. By way of example, "an element" means at least one element and can include more than one element. "About" is used to provide flexibility to a numerical range endpoint by providing that a given value may be "slightly above" or "slightly below" the endpoint without affecting the desired result. The use herein of the terms "including," "comprising," or "having," and variations thereof, is meant to encompass the elements listed thereafter and equivalents thereof as well as additional elements. As used herein, "and/or" refers to and encompasses any and all possible combinations of one or more of the associated listed items, as well as the lack of combinations where interpreted in the alternative ("or"). Moreover, the present disclosure also contemplates that in some embodiments, any feature or combination of features set forth herein can be excluded or omitted. To illustrate, if the specification states that a system or device comprises components A, B and C, it is specifically intended that any of A, B, or C, or any combination thereof, can be omitted and disclaimed singularly or in any combination, including but not necessarily with other components (e.g., D, E, etc.).

Recitation of ranges of values herein are merely intended to serve as a shorthand method of referring individually to each separate value falling within the range, unless otherwise indicated herein, and each separate value is incorporated into the specification as if it were individually recited herein. For example, if a concentration range is stated as 1% to 50%, it is intended that values such as 2% to 40%, 10% to 30%, or 1% to 3%, etc., are expressly enumerated in this specification. These are only examples of what is specifically intended, and all possible combinations of numerical values between and including the lowest value and the highest value enumerated are to be considered to be expressly stated in this disclosure. Unless otherwise defined, all technical terms used herein have the same meaning as commonly understood by one of ordinary skill in the art to which this disclosure belongs.

Wearable Optical Device Examples

Figures 1B, 1C:
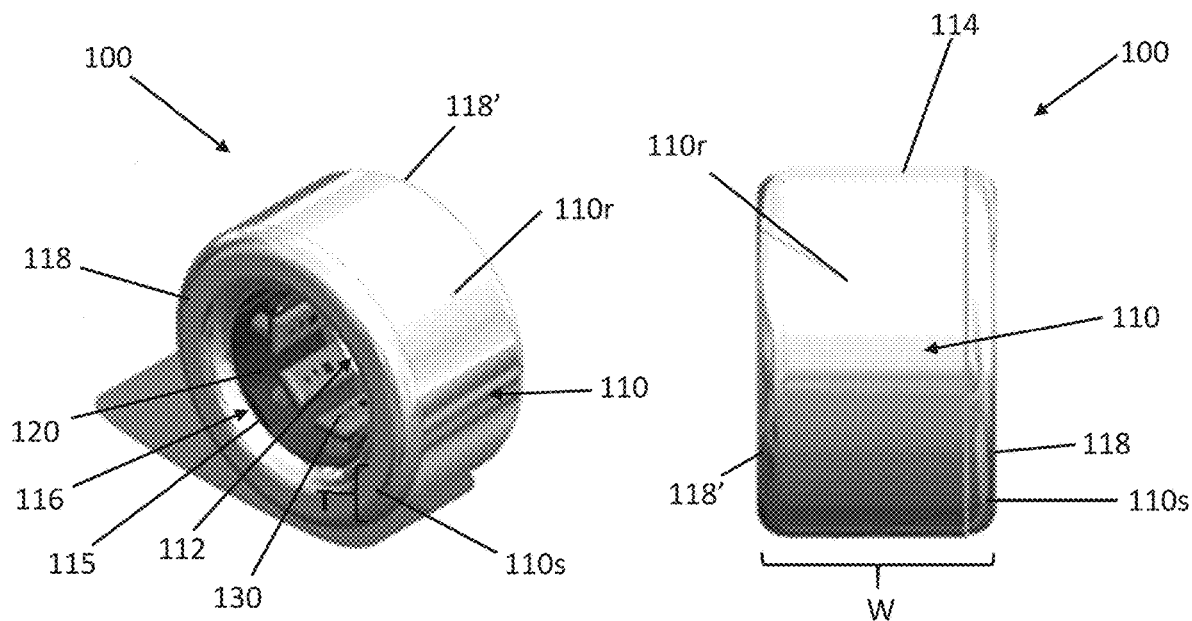
FIG. 1B is an isometric side view of the wearable optical device of FIG. 1A.
FIG. 1C is a side view of the wearable optical device of FIG. 1A.

One embodiment of a wearable optical device of the present disclosure is illustrated in FIGS. 1A-1C. FIG. 1A shows a side view of a wearable optical device 100 with a plurality of sensor assemblies 130 positioned within the circumference. Each sensor assembly 130 is configured to measure at least one biosignal. Wearable optical devices of the present disclosure can be generally circular and sized and shaped such that they can be worn comfortably on an appendage of a subject (e.g., a finger or toe). For example, the device 100 of FIGS. 1A-1C is a circular ring shape defining a central opening 112 sized and shaped to receive a finger or other appendage. In other embodiments, the device can be sized to be worn around a wrist. The device 100 includes an outer case 110. The outer case 110 is ring shaped and defines an outer surface 114 and an inner surface 115 opposing the outer surface 114. The inner surface 115 is configured to face the skin when worn on an appendage. A recess 116 can be formed within the inner surface 115 and can be configured to receive electronics or other components. The outer case can include two edges, 118, 118' joining the outer surface 114 and the inner surface 115. The edges 118, 118' can be curved or beveled. When the device 100 is worn on an appendage, the edges 118, 118' contact the skin surface enclosing the space within the recess 116 between the skin, the outer case 110, and edges 118, 118'. As shown in FIG. 1B, a carrier 120 can be disposed within the inner recess 116 of the outer case 110. The carrier 120 is sized and shaped to fit within the recess of the outer case 110 and configured to secure each sensor assembly 130 within the device 110 at the appropriate position. The outer case 110 has a width W and thickness T sufficient to house internal components while also maintaining a slim profile allowing the device to be comfortably worn on an appendage during daily activities.

Figure 2A:
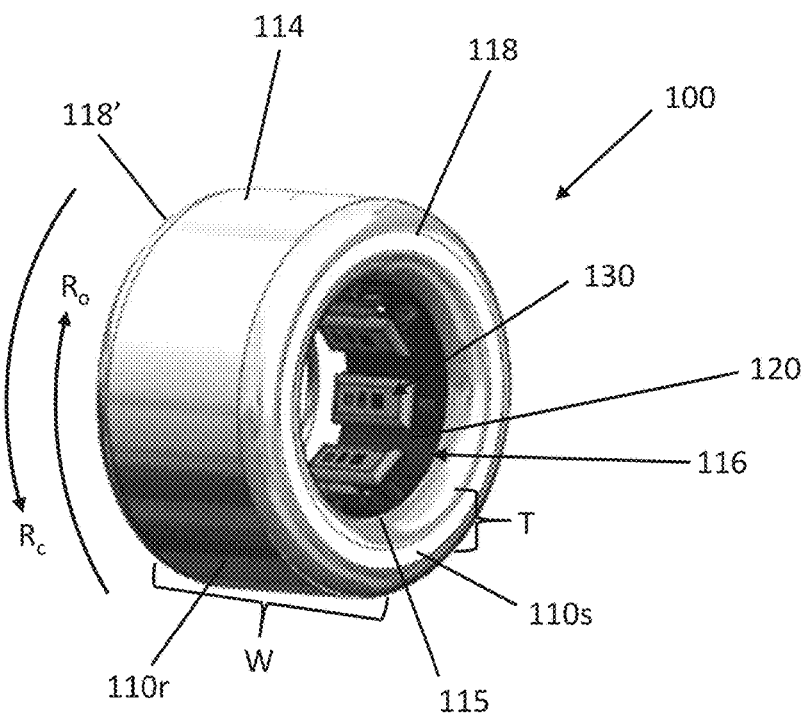
FIG. 2A is an isometric side view of a wearable optical device with a radial adjustment mechanism.
Figure 2B:
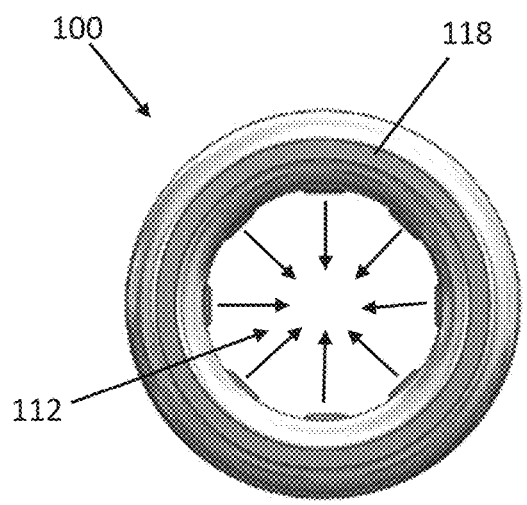
FIG. 2B is a front view of the wearable optical device of FIG. 2A in an open configuration.
Figure 2C:
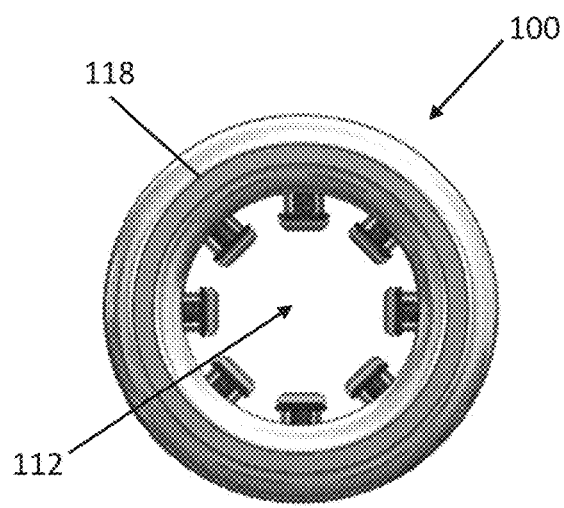
FIG. 2C is a front view of the wearable optical device of FIG. 2A in a closed configuration.

In some embodiments, the outer case 110 can be radially adjustable as shown in FIG. 2A. The adjustability includes movement of the device 100 from an open configuration shown in FIG. 2B to a closed configuration shown in FIG. 2C. In the open configuration, the sensors 130 are in a retracted position that is proximal to the carrier 120 and the outer case 110. In the closed configuration, the sensor assemblies 130 are in an extended position (e.g., by being moved towards the centerpoint of the central opening 112). Returning to FIG. 2A, the outer case 110 can include two sections 110s, 110r rotatably coupled to each other. The stationary section 110s can be fixed to the carrier 120 while the rotatable section 110r is free to rotate around the carrier 120. The rotatable section 110r can comprise a majority of the width W of the outer case 110 while the stationary section 110s comprises an edge of the outer case 110 and a portion of the width W. A cam mechanism can be disposed between the outer case 110 and the carrier 120 such that when the second section 110r of the outer case is rotated in a first direction $R_o$, the sensor assemblies 130 are extended towards the centerpoint of the central opening 112. Inversely, rotating the second section 110r of the outer case in an opposing direction $R_c$ retracts the sensor assemblies 130 back towards the carrier 120. Any mechanism capable of translating rotational movement to axial movement can be used to extend and retract the sensor assemblies 130 of the present disclosure.

Figure 3A:
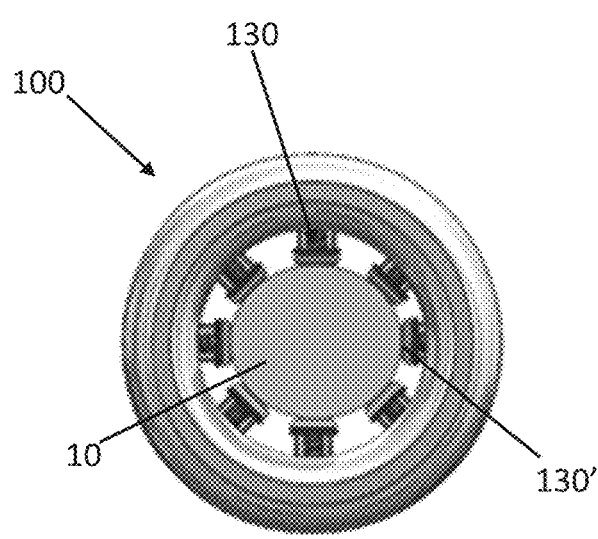
FIG. 3A is a front view of one exemplary embodiment of a wearable optical device worn on an appendage.
Figure 3B:
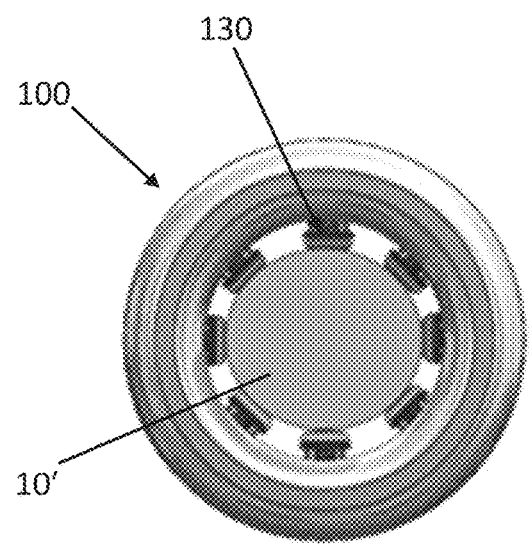
FIG. 3B is a front view of one exemplary embodiment of a wearable optical device worn on an appendage.
Figure 3C:
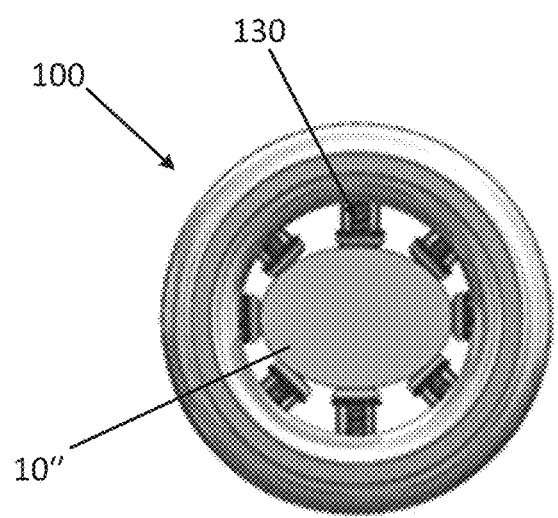
FIG. 3C is a front view of one exemplary embodiment of a wearable optical device worn on an appendage.
Figure 3D:
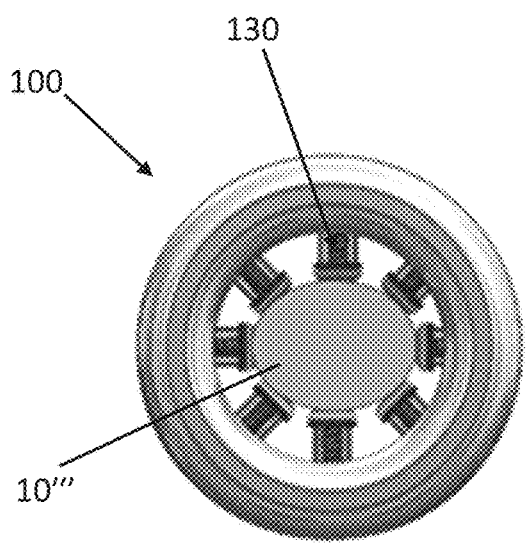
FIG. 3D is a front view of one exemplary embodiment of a wearable optical device worn on an appendage.
Figure 6A:
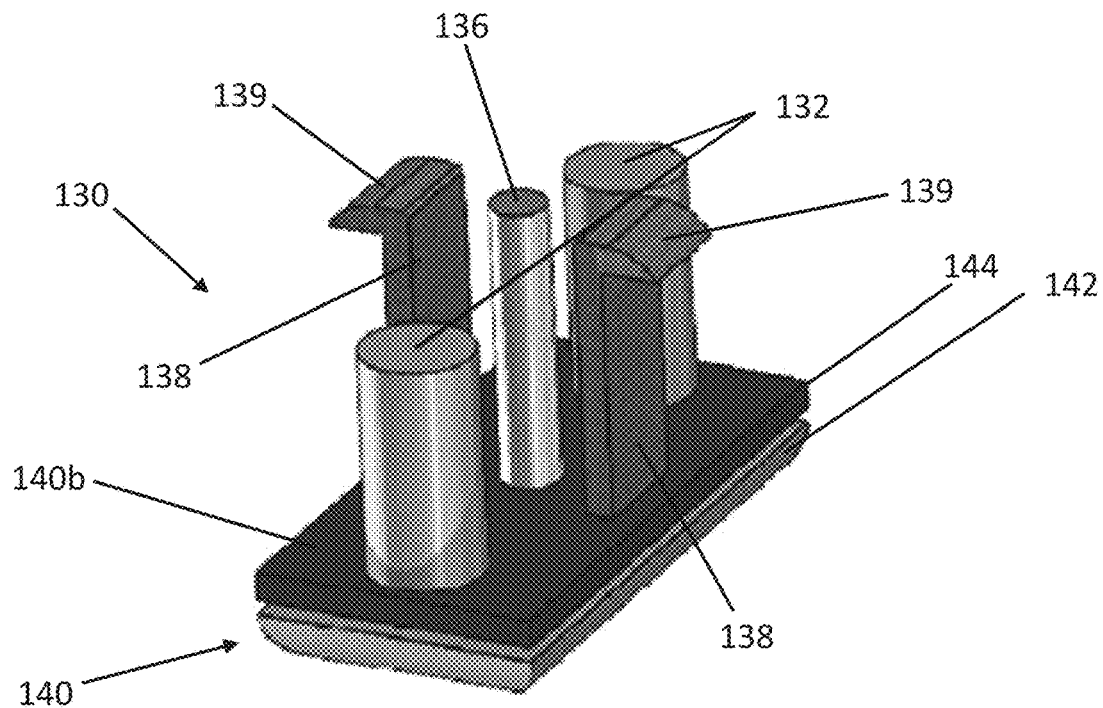
FIG. 6A is an isometric side view of one exemplary embodiment of a sensor assembly.
Figure 6B:
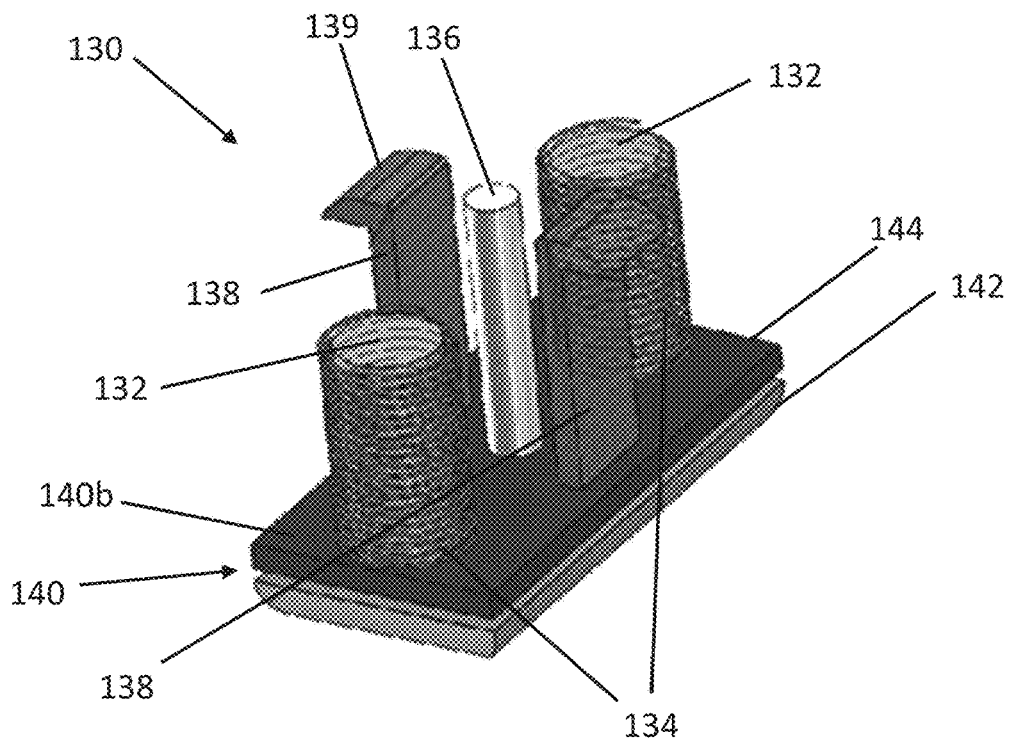
FIG. 6B is an isometric side view of the sensor assembly of FIG. 6A including tension springs.

As discussed with respect to FIG. 6B, each sensor assembly 130 can include a biasing mechanism, or other component capable of applying controlled tension, to ensure each sensor assembly 130 is pressed against the appendage when the device 100 is worn in the closed position and the sensor assemblies 130 are extended. The biasing mechanism maintains contact of the sensor assemblies 130 on appendages of varying sizes and geometries. For example, the device 100 can accommodate an appendage 10 with an irregular circular shape as shown in FIG. 3A. With this shape, some of the sensor assemblies such as sensor assembly 130' can contact the appendage at a shorter distance from the outer case 110 than the other sensor assemblies such as sensor assembly 130. FIG. 3B shows an example of the device 100 placed on a larger appendage 10'. FIG. 3C shows the device 100 placed on an elliptical shaped appendage 10" and FIG. 3D shows the device placed on an irregular elliptical shaped appendage 10'''. In all of the examples of FIGS. 3A-3D, all of the sensor assemblies 130 contact the appendage regardless of the shape or size of the appendage.

Figure 4A:
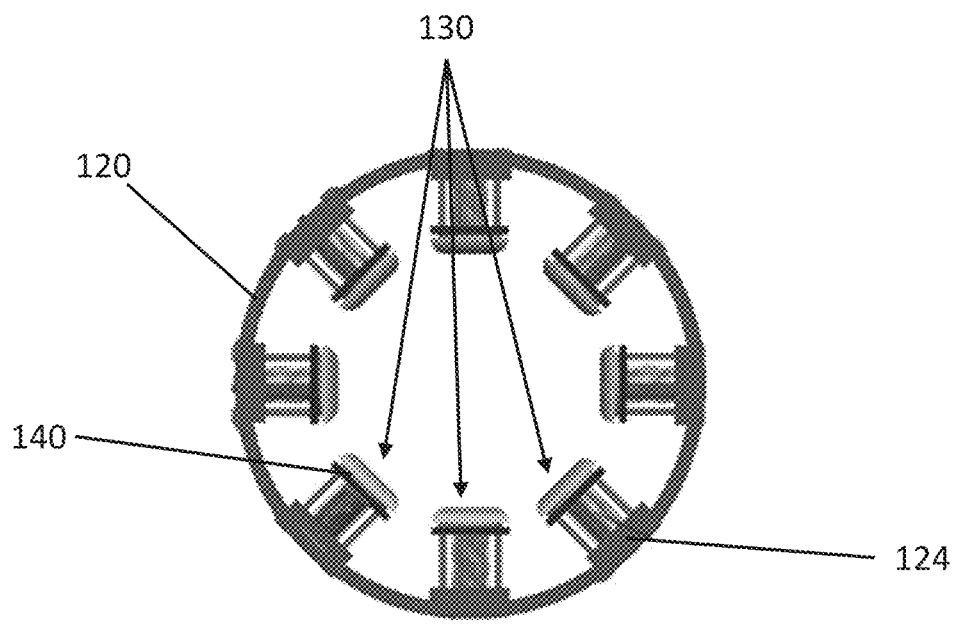
FIG. 4A is a side view of one exemplary embodiment of a sensor carrier with sensors disposed within the carrier.
Figure 4B:
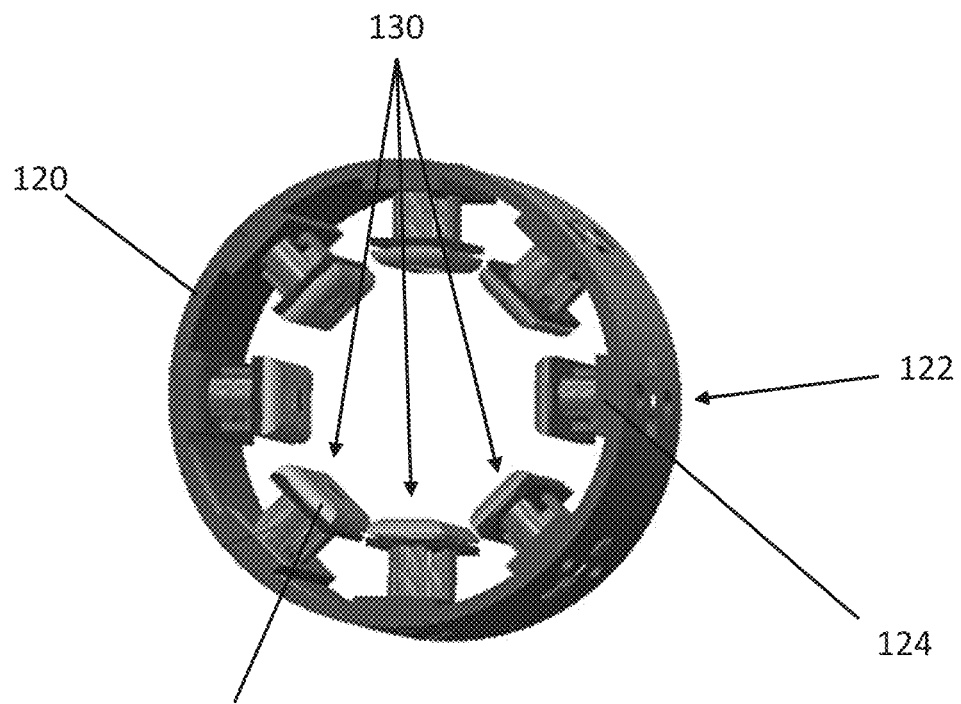
FIG. 4B is an isometric side view of the sensor carrier of FIG. 4A.

An embodiment of a sensor carrier 120 that can be disposed within the outer case 110 is illustrated in FIGS. 4A and 4B. As shown, the carrier 120 is a relatively flat ring shaped component sized to fit within the recess 116 of the outer case 110. In both of the open and closed configurations shown in FIGS. 2B and 2C, the carrier is configured to fit completely within the recess of the outer case such that no portion of the carrier extends beyond the recess 116 and into the central opening 112. The carrier 120 can include coupling features 122 along its circumference to secure each sensor assembly 130. In the illustrated example of FIG. 4B, the coupling features 122 are openings configured to receive retainer clips 138 included on the sensor assembly 130 as well as openings to receive guide pins, position sensors, or other components of the sensor assemblies 130 (as shown in FIGS. 6A and 6B). The coupling features 122 can be formed within mounts 124 extending from the inner surface of the carrier 120.

Figure 5:
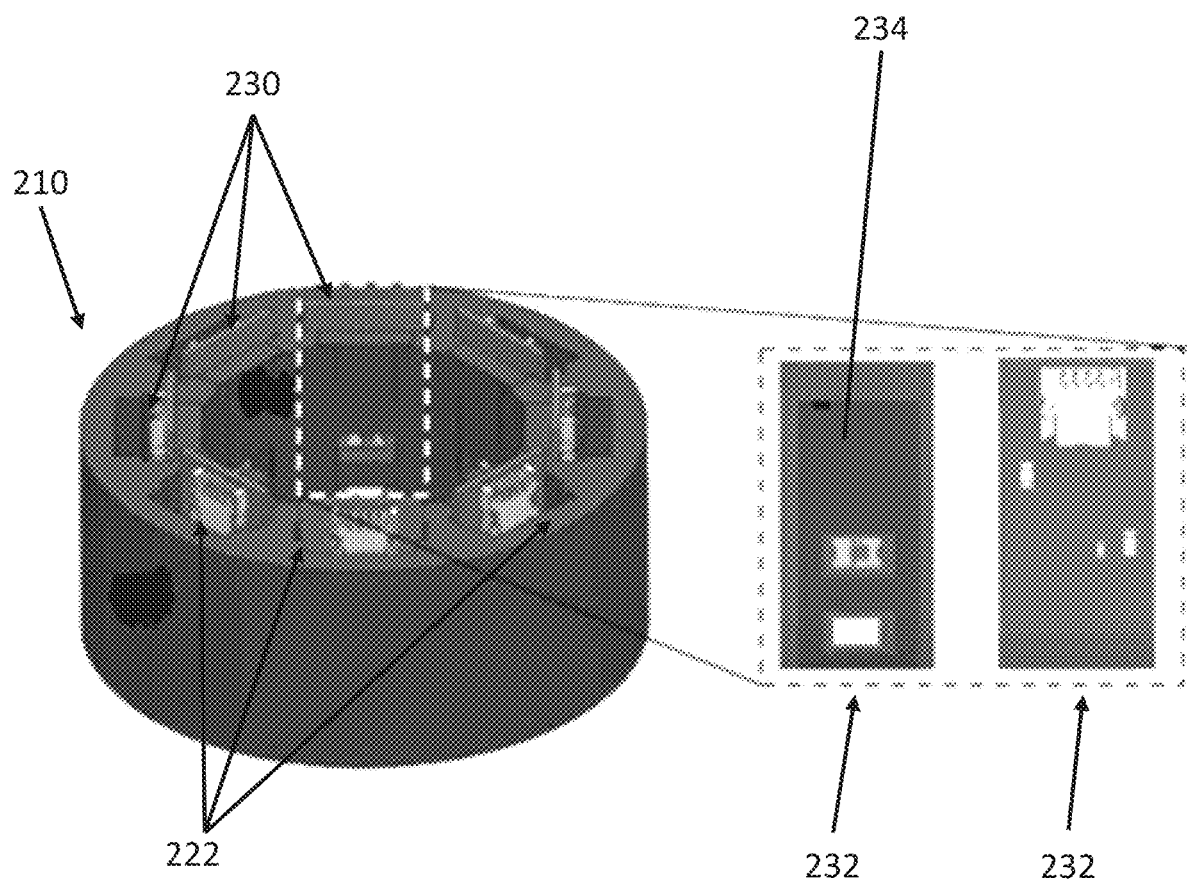
FIG. 5 is an isometric side view of another exemplary embodiment of a wearable optical device.

In some embodiments, the sensor assemblies 230 are coupled directly to the outer case 210 as show in FIG. 5. As illustrated, the sensor assembly 230 includes a circuit board 232 secured in slots 222 formed within the outer case 210. A cover 234 is placed over the sensor circuit boards 232 in each slot 222 to prevent signal interference between each sensor assembly 230.

Sensor Arrangement Examples

Examples of the present disclosure include sensor assemblies configured to detect and measure signals suitable for calculating physiological parameters, such as heart rate, heart rate variability, respiration rate, and blood oxygenation. The sensor assemblies disclosed herein include a light source, such as a light-emitting diode (LED), and a light detector, such as a photodiode (PD), each typically mounted to a printed circuit board for sending and receiving electrical signals to and from a central circuit board disposed within the device 100. An embodiment of a sensor assembly 130 that can be disposed within the device 100 is illustrated in FIGS. 6A-6B. The illustrated sensor assembly 130 includes a sensor interface 140, which includes the light source and detector (shown in FIG. 7A). The sensor assembly 130 can further include two or more guide pins 132 extending from the back surface 140b of the sensor interface 140. In the example illustrated in FIG. 6A, two guide pins 132 are fixed along the length of the interface 140 at a perpendicular angle to the back surface 140b to keep the sensor interface 140 aligned at a perpendicular angle relative to the carrier 120 as the device 100 moves from an open to a closed configuration. A biasing mechanism, such as tension springs 134 can be disposed around the guide pins 132 to bias the sensor interface 140 towards the appendage. The sensor assembly 130 further includes a position sensor 136 disposed on the back surface 140b of the sensor interface 140 and operably coupled to the central circuit board. The position sensor 136 can be coupled to the sensor interface 140 such that, in operation, the position sensor 136 detects and measures the radial distance of the sensor interface 140 from the center point of central opening 112. As discussed with respect to FIGS. 4A and 4B, the guide pins 132 and position sensor 136 are disposed within openings of the carrier 136 and configured to move within the openings as the device 100 moves from an open to a closed configuration. Coupling features 138, corresponding to the coupling features of the carrier 120 can be included in the sensor assembly 130. In the example of FIGS. 6A and 6B, the coupling features are retainer clips 138 fixed to the back surface 140b of the sensor interface 140. Each retainer clip 138 extends perpendicular from the back surface 140b and contains a tab 139 at the distal-most end. The retainer clip 138 is configured to pass through an opening formed in the carrier 120 while the tab is configured to contact the outer surface of the carrier to limit the movement of the sensor interface 140 past a certain distance from the carrier 120. Any other coupling mechanism know in the art can be used to couple the sensor assemblies 130 to the carrier 120.

Figure 7A:
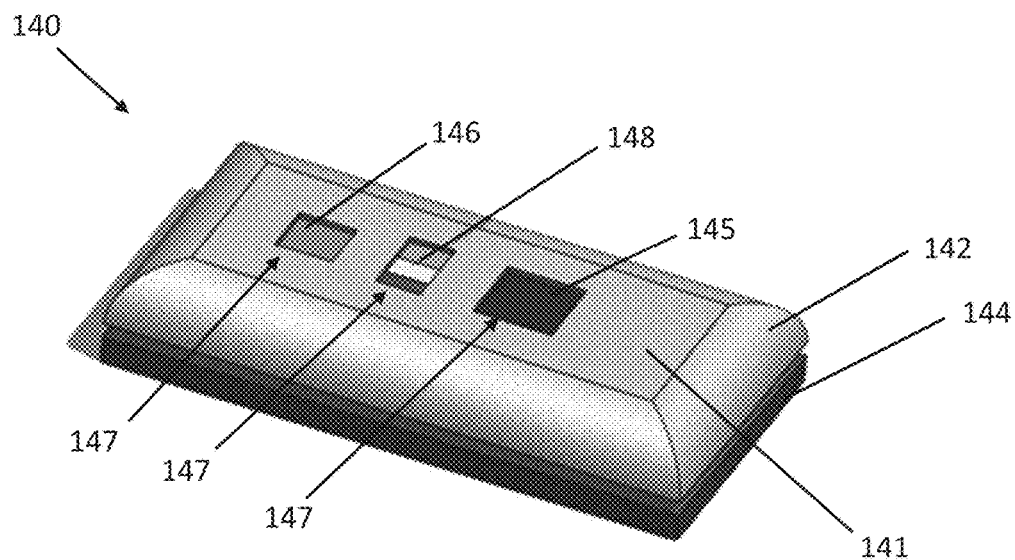
FIG. 7A is an isometric top view of one exemplary embodiment of a sensor interface.
Figure 7B:
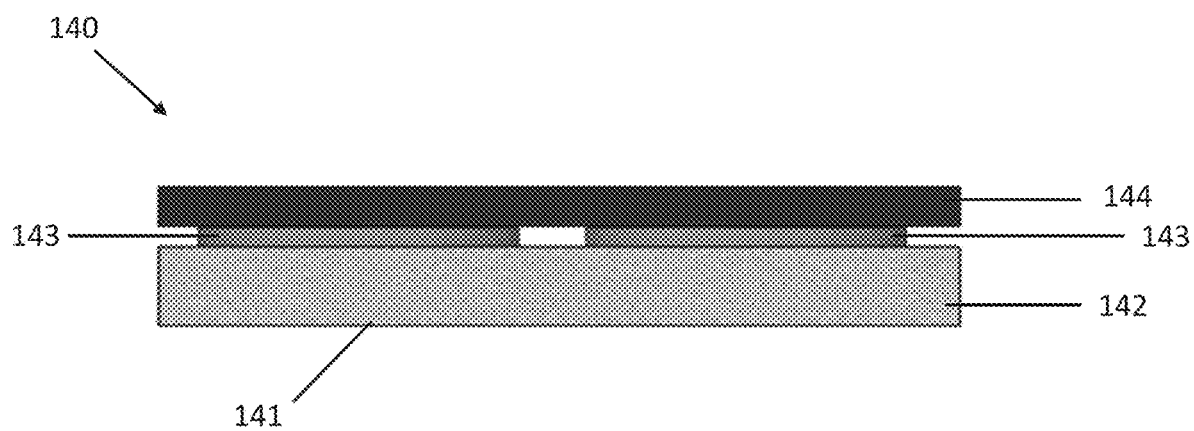
FIG. 7B is a side view of the sensor interface of FIG. 7A.

An example of a sensor interface 140 is illustrated in FIGS. 7A-7B. In some embodiments, the sensor interface 140 is the printed circuit board to which the light source and photodiode are mounted, in other embodiments, the sensor includes a housing 141 configured to house the light source 148 and the detector 145. The housing 142 can include a contact surface 141. The sensor assemblies can each comprise additional sensors operably connected to the central circuit board. For example, as shown in FIGS. 7A and 7B, a pressure transducer 143 and an associated receiver 144 are coupled to the housing 141 and configured to quantify the force of pressure between the skin and the sensor interface 140. A temperature sensor 146 is mounted to the printed circuit board disposed within the housing 141 to measure the temperature of the appendage. Electrical components, such as the printed circuit board, are disposed within the housing such that contact surfaces of the light source 148, detector 145, and temperature sensor 146 contact the appendage. A plurality of openings 147 can be formed on the contact surface 141 of the housing 142 to allow contact surfaces of an LED 148, photodiode 145, or other sensor 146 disposed on the printed circuit board to contact the appendage.

The printed circuit board can be disposed within the housing 142 between the contact surface 141 and pressure transducer 143. In some embodiments, the housing 142 can fully enclose the printed circuit board or the printed circuit board as well as the pressure transducer 143 and receiver 144.

The light source 148 can be a LED array including green, red or infrared LEDs or any LED with a wavelength between about, for example, 400 nm and 1500 nm. Biological materials within the appendage absorb light of varying wavelengths. Using an array of varying LEDs allows the device 100 to capture an accurate signal from each material. For example, water and lipids absorb wavelengths beyond 1000 nm better than wavelengths below 1000 nm and blood absorbs wavelengths between 400 nm and 600 nm. Each detector 145 can be a single photodiode (PD) or a PD array, each configured to perform in a frequency range corresponding to the emitted frequencies from the light sources, for example, between 400 nm and 1500 nm (e.g., corresponding to the wavelengths of the LEDs 148). Each PD 145 can be configured to measure signals in both reflective and transmittance modes. In embodiments where the light source 144 and the detectors 145 are mounted to a printed circuit board, the printed circuit board further includes an analog front end configured to acquire and condition the signals detected by the detectors 145. In some examples, the analog front end includes a transimpedance amplifier, a buffer, and other signal amplification circuits and does not include analog filters. The absence of analog filters preserves the raw acquired signals, thereby allowing the integrity of the AC and DC components of the signals to be captured and used for processing.

Signal Acquisition and Signal Processing Examples

Figure 8A:
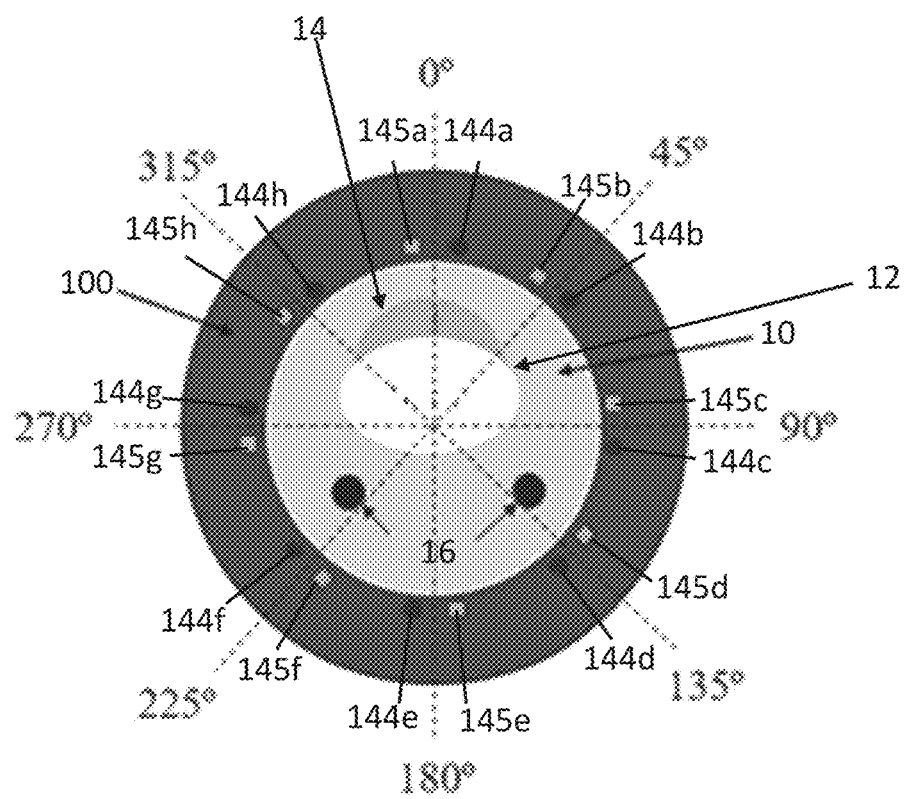
FIG. 8A is a schematic of LED and PD alignment around the circumference of an optical device worn on a proximal phalanx with an estimate of the location of the major anatomical components within the phalanx.

An example schematic of sensor assembly position of the previously disclosed device is illustrated in FIG. 8A. In the illustrated example, eight sensor assemblies are positioned at 45° intervals around the circumference of the device 100. Each sensor assembly incudes a LED 144a-h and a PD 145a-h. Any number of sensor assemblies between can be positioned within the circumference of the device at equal intervals around the inner circumference, though advantageously 3 or more are used to enable improved special reconstruction. Each assembly can lie on the same radial axis as an opposing assembly. The alignment of the sensor assemblies allows the device to measure signals in transmission mode, where the LED and PD are on the opposite sides of the subject, or reflective mode, where the LED and PD are on the same side of the subject.

Figure 8B:
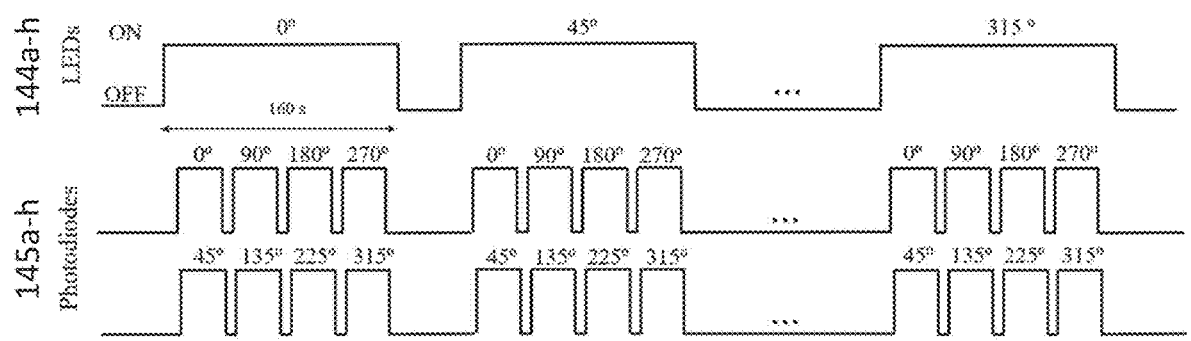
FIG. 8B is a diagram of one exemplary embodiment of a timing scheme for use in conjunction with the present disclosure.

An exemplary timing scheme for acquiring signals using the device 100 of the present disclosure is illustrated in FIG. 8B. In general, the LEDs can be illuminated individually in sequential order. When a single LED is illuminated, pairs of photodiodes are sequentially sampled until all LEDs have been turned on and all photodiode pairs are samples for each LED. For example, in a device with eight sensor assemblies as shown in FIG. 9A, a first LED 144a positioned at the 0° position is illuminated for approximately 160 seconds. While the first LED 144a is illuminated, pairs of photodiodes positioned on the same axis are sampled sequentially. In the present example, a pair of photodiodes 145a, 145b positioned at the 0° and 45° are sampled, then photodiodes 145c, 145d positioned at 90° and 135°; photodiodes 145e, 145f positioned at 180° and 225°; and photodiodes 145g, 145h positioned at 270° and 315° are sequentially sampled after. In a representative and non-limiting example, each photodiode pair can be sampled for approximately 40 seconds. Once all of the photodiode pairs are sampled, the first LED at the 0° position is turned off and the next LED positioned at the 45° position is illuminated and each pair of LEDs sampled for the first LED are again sequentially sampled for the next LED. The process continues until all LEDs are individually illuminated and each photodiode pair is sampled. In an embodiment of a device with eight sensors, this process results in 64 total signals. The process can be repeated for each wavelength LED of the PPG sensors.

In some embodiments, the PDs are sampled individually instead of in pairs. For example, while the LED 144a at the 0°, each of the PDs 145a-h can be sampled individually, all of the PDs can be sampled simultaneously, or any number of PDs can sampled simultaneously. Once all of the PDs are sampled, the LED 144a can be turned off, and the next LED 144b is illuminated and all PDs 145a-h are sampled. Although examples where the LEDs and PDs are illuminated and sampled sequentially in order of placement around the device are discussed, the LEDs and PDs can be illuminated and sampled in any order until a signal from each combination of LED and PD is acquired.

Figure 9:
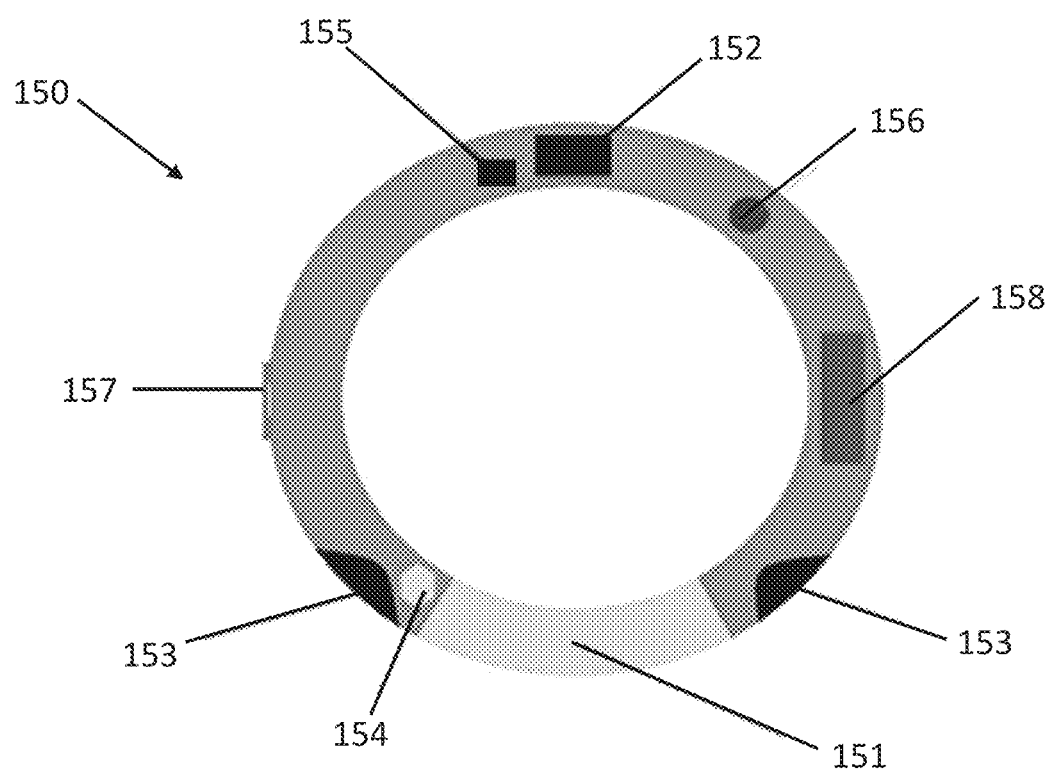
FIG. 9 is a schematic of one exemplary embodiment of a central circuit board.

The printed circuit boards of each sensor can be connected to a central circuit board 150 configured to control the signal acquisition. An exemplary embodiment of a central circuit board 150 is illustrated in FIG. 9. The illustrated central circuit board 150 can include a computing system such as a microcontroller 152. The microcontroller can contain instructions for the device to acquire the desired signals. The central circuit board 150 can include a battery 151 to provide power to the device. The battery can be rechargeable through the use of charge inductors 153 and a charge circuit 154. The central circuit 150 board can include a data storage module configured to store signals or data for further processing at a later time. The central circuit board 150 can further include a Bluetooth or Wi-Fi module 156 configured to transfer data from the device to a computing system or transfer instructions from the computing system to the device 100. In some embodiments, the central circuit board 150 can include one or more additional sensors to acquire additional parameters such as an ambient temperature sensor 157, or a gyroscope, an accelerometer, and a magnetometer 158 to sense position and movement of the device 100.

Figure 10:
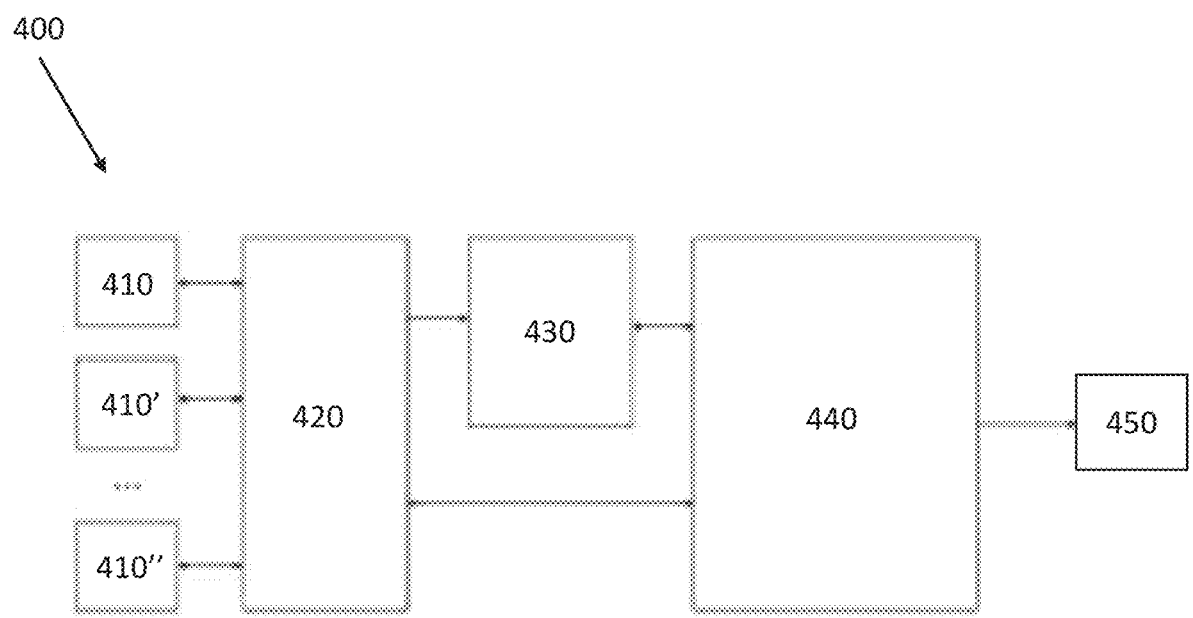
FIG. 10 is a block diagram of one exemplary embodiment of a circuit system for use within the devices of the present disclosure.

FIG. 10 is a block diagram of an exemplary system 400 of the device 100. In this example, the analog front end 410 of each sensor circuit board acquires and conditions a signal from the appendage and sends the signal to the central circuit board through a connection unit 420. The signal can then be passed through an analog-to-digital converter (ADC) 430 and then to a microcontroller 440. An ADC 430 with a resolution high enough to produce a waveform with distinguishable AC and DC components can be used. The microcontroller 440 can be configured to sample and control all LEDs and PDs within the sensor assemblies. For example, the microcontroller can be programmed with a timing scheme, such as the scheme of FIG. 8B, to illuminate each LED and sample the signals from each PD. In a device with eight sensor assemblies, the microcontroller can acquire 64 signals at a sampling rate, for example, at a minimal of 200 Hz. In some examples, a signal to noise ratio (SNR) of the system 400 is at least 5:1. The microcontroller 440 can then send the data to a computing device or system 450 for further processing. The computing system 450 can contain instructions to process the signals and provide real-time information as discussed below.

While examples shown herein include certain circuit components, these are representative and one skilled in the art will appreciate that these specific components can be replaced by functionally equivalent parts, as well as other versions with corresponding changes incorporated to the circuits to utilize them in an effectively similar manner to those presented herein.

The signals acquired by the devices of the present disclosure can be processed to obtain various static and dynamic measurements. The signals can be processed by software or a code of instructions located on a computing system 450. The computing system 450 can be a personal computer, or a handheld device such as a cell phone. In some embodiments, the device can be used in a clinical setting in conjunction with a larger computing system 450. The below actions can be done on either the computing system or ring device or some combination of both.

To measure physiological signals such as heart rate, heart rate variability, respiration, and blood oxygenation, the acquired data can be filtered and processed to extract the AC component and quasi-DC component (i.e. zero and very low frequency) of the signal. A low pass filter can be used to remove high-frequency noise from the raw signal. In some embodiments, a low pass filter with a cutoff of 5-10 Hz can be used. The AC component makes up the pulsatile arterial blood signal, while the quasi-DC component comprises signals originating from bone, tissue, venous blood, non-pulsatile arterial blood, and other tissue matter. Heart rate and heart rate variability can be derived from the AC component of the PPG signal, while respiration and blood oxygenation can be derived from the AC and quasi-DC components. The AC and quasi-DC components of the filtered signal can be separated by isolating the quasi-DC component using an envelope filter and subtracting the DC component from the filtered data, thus, isolating the AC component The signals can be further processed using diffuse optical tomography (DOT) techniques to reconstruct a 2D or 3D image of the inner appendage to provide additional information about the static and dynamic signals. Accurate imaging of the inner appendix can provide the ability to isolate areas of interest within the appendage such as the main artery or superficial vessels.

Examples include the use of a continuous-wave DOT approach for near real-time imaging of the inner appendage. Various additional methodologies can be used to build an image reconstruction algorithm. Examples include reconstructions based on Rosenbrock's banana function, back projections, Monte Carlo simulations, machine-learning models, and other techniques known to one skilled in the art.

The mentioned reconstruction, or inverse, techniques are advantageous as computationally inexpensive approaches capable of giving metrics in real-time. Rosenbrock's banana function, back projections, and Monte Carlo simulations are relatively computationally inexpensive since the approaches taken can "smear" or project signal from the light source to the appropriate detector following an estimated path. The path can be estimated using the modified beer-lambert law and the diffuse equation. Interpolation image processing techniques can also be paired with a reconstruction algorithm to optimize resolution of the images further.

Machine Learning Examples

Examples of the present disclosure include the use of deep learning models to increase efficiency of the reconstruction techniques while also providing the ability to potentially train a model unsupervised based on in vivo data. The use of deep learning models can increase image resolution by taking a low-resolution image and recovering a high-resolution image through a technique referred to as super-resolution.

Examples include the use of a deep convolutional neural network that is configured to take an initial image estimate and optimize the resolution to enable hemoglobin and blood volume concentrations to be accurately identified. Example algorithms can reconstruct a single image to a higher resolution image and/or multiple images. In these examples, transfer learning can be employed to train the neural network using an existing datasets. In some embodiments, the algorithm is trained through unsupervised learning. Additionally, interpolation can be utilized to increase the resolution of collected images. Example interpolation methods can include but are not limited to nearest neighbor, bilinear, bicubic, or cubic B-spline interpolation.

Additional Embodiments

Some exemplary methods disclosed can use two synced optical devices 100 of the present disclosure to acquire additional physiological measurements such pulse wave velocity. Two synced devices can be used or a single device, such as the device 100 can be modified to include two sensor carriers within a single outer case, each sensor carrier housing a row of sensor assemblies in a ring formation around the appendage, the rows of sensors parallel to each other. Pulse wave velocity can be calculated by measuring the time it takes the arterial pulse to travel a specific distance and then dividing the distance by the transit time. A first ring can send a radiofrequency wave to a second device. The time it takes for the wave to travel is divided by the wave speed to find the distance between the two devices. In other embodiments, a first ring can send a radiofrequency wave to a second ring and receive a reflected radio frequency wave back from the second ring. The arrival time is divided by 2 to find the distance between the two devices. In some methods, two rings can be placed on an appendage. The pulse wave velocity can then be determined using the distance between the devices and the signal arrive times for each device. In some method example, a single ring device can be used in conjunction with an armband instead of a second a ring device.

A charging platform can be provided with the devices of the present disclosure. The charging platform can function wired or wireless. In some embodiments, the charging platform can also function as a syncing platform to synchronize a plurality of devices for the purposes described above.

In some embodiments, the ring devices of the present disclosure include a single light source and fiber optic cables configured to transfer the light emitting from the light source to a plurality of locations. One with skill in the art with appreciate that any configuration capable of directing light to a location can be used in the device of the present disclosure.

In some embodiments, the ring devices of the present disclosure can be electrically connected to external equipment in a clinical setting to provide additional power to the device and computing to process more complicated signals. In these embodiments, the light sources can be connected fiber optic cables to direct light to the appendage. The main circuit board of the device or the sensor circuit boards can be electrically coupled to a computing system containing instructions to process the signals and provide information in real-time.

Figure 11:
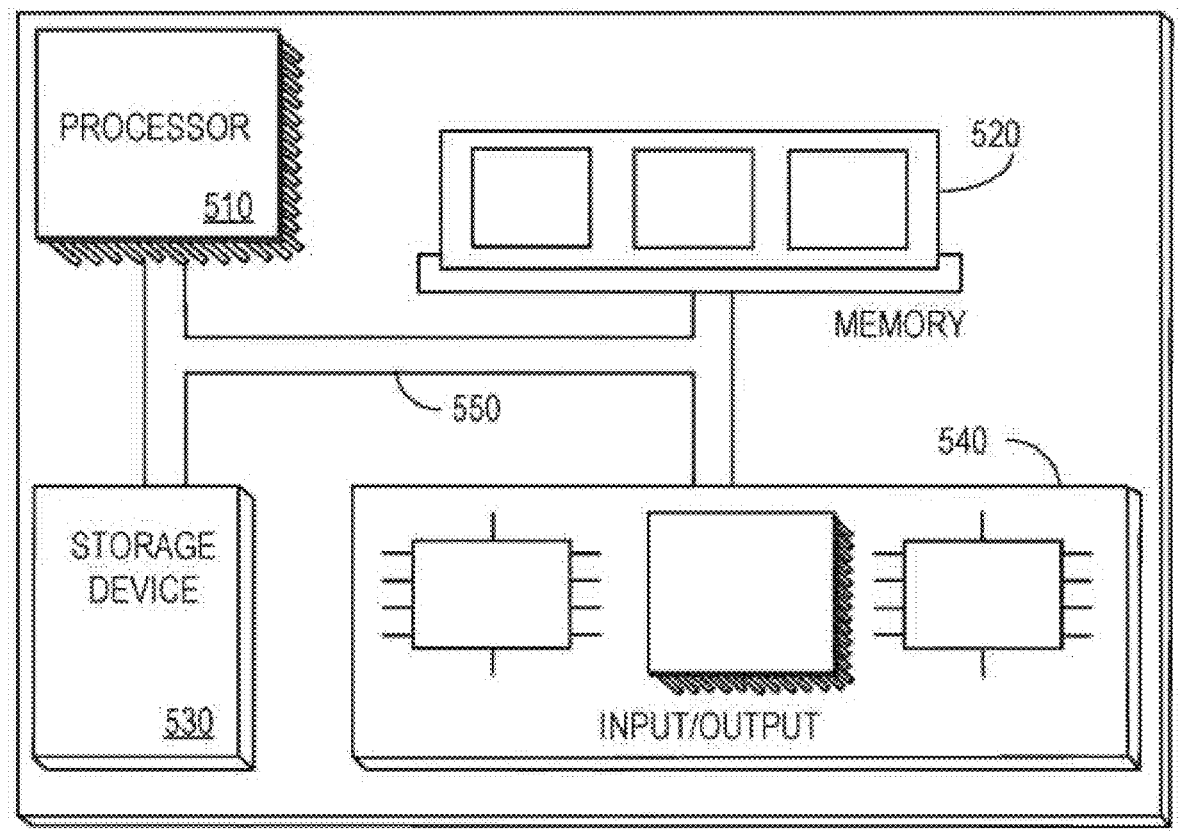
FIG. 11 is a block diagram of one exemplary embodiment of a computer system for use in conjunction with the present disclosure.

FIG. 11 provides for one non-limiting example of a computer system 1400 upon which the present disclosure can be built, performed, trained, etc. For example, referring to FIGS. 9 and 10, the processing modules or processors 450 can be examples of the system 500 described herein. The system 500 can include a processor 510, a memory 520, a storage device 530, and an input/output device 540. Each of the components 510, 520, 530, and 540 can be interconnected, for example, using a system bus 550. The processor 510 can be capable of processing instructions for execution within the system 500. The processor 510 can be a single-threaded processor, a multi-threaded processor, or similar device. The processor 510 can be capable of processing instructions stored in the memory 520 or on the storage device 530. The processor 510 may execute operations such as calculation of a turbulence transition mode, calculation of a flow disturbance to suppress a turbulence transition mode, or adjustment of a predicted turbulence transition mode based on information received from one or more sensors measuring a fluid flow, among other features described in conjunction with the present disclosure, including any control logic associated with the operation of an active turbulence suppression system or device.

The memory 520 can store information within the system 500. In some implementations, the memory 1420 can be a computer-readable medium. The memory 520 can, for example, be a volatile memory unit or a non-volatile memory unit. In some implementations, the memory 520 can store information related conduit geometries, fluid flow parameters (predicted or measured), turbulence transition mode(s), any information related to the calculation of the turbulence transition mode, among other information.

The storage device 530 can be capable of providing mass storage for the system 500. In some implementations, the storage device 530 can be a non-transitory computer-readable medium. The storage device 530 can include, for example, a hard disk device, an optical disk device, a solid-date drive, a flash drive, magnetic tape, or some other large capacity storage device. The storage device 530 may alternatively be a cloud storage device, e.g., a logical storage device including multiple physical storage devices distributed on a network and accessed using a network. In some implementations, the information stored on the memory 520 can also or instead be stored on the storage device 530.

The input/output device 540 can provide input/output operations for the system 500. In some implementations, the input/output device 540 can include one or more of network interface devices (e.g., an Ethernet card), a serial communication device (e.g., an RS-232 10 port), and/or a wireless interface device (e.g., a short-range wireless communication device, an 802.11 card, a 3G wireless modem, or a 4G wireless modem). In some implementations, the input/output device 1440 can include driver devices configured to receive input data and send output data to other input/output devices, e.g., a keyboard, a printer, and display devices. In some implementations, mobile computing devices, mobile communication devices, and other devices can be used.

In some implementations, the system 500 can be a microcontroller. A microcontroller is a device that contains multiple elements of a computer system in a single electronics package. For example, the single electronics package could contain the processor 510, the memory 520, the storage device 530, and input/output devices 540.

Although an example processing system has been described above, implementations of the subject matter and the functional operations described above can be implemented in other types of digital electronic circuitry, or in computer software, firmware, and/or hardware, including the structures disclosed in this specification and their structural equivalents, or in combinations of one or more of them. Implementations of the subject matter described in this specification can be implemented as one or more computer program products, i.e., one or more modules of computer program instructions encoded on a tangible program carrier, for example a computer-readable medium, for execution by, or to control the operation of, a processing system. The computer readable medium can be a machine-readable storage device, a machine-readable storage substrate, a memory device, a composition of matter effecting a machine-readable propagated signal, or a combination of one or more of them.

Various embodiments of the present disclosure may be implemented at least in part in any conventional computer programming language. For example, some embodiments may be implemented in a procedural programming language (e.g., "C"), or in an object-oriented programming language (e.g., "C++"). Other embodiments of the invention may be implemented as a pre-configured, stand-along hardware element and/or as preprogrammed hardware elements (e.g., application specific integrated circuits, FPGAs, and digital signal processors), or other related components.

The term "computer system" may encompass all apparatus, devices, and machines for processing data, including by way of example a programmable processor, a computer, or multiple processors or computers. A processing system can include, in addition to hardware, code that creates an execution environment for the computer program in question, e.g., code that constitutes processor firmware, a protocol stack, a database management system, an operating system, or a combination of one or more of them.

A computer program (also known as a program, software, software application, script, executable logic, or code) can be written in any form of programming language, including compiled or interpreted languages, or declarative or procedural languages, and it can be deployed in any form, including as a standalone program or as a module, component, subroutine, or other unit suitable for use in a computing environment. A computer program does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

Such implementation may include a series of computer instructions fixed either on a tangible, non-transitory medium, such as a computer readable medium. The series of computer instructions can embody all or part of the functionality previously described herein with respect to the system. Computer readable media suitable for storing computer program instructions and data include all forms of non-volatile or volatile memory, media and memory devices, including by way of example semiconductor memory devices, e.g., EPROM, EEPROM, and flash memory devices; magnetic disks, e.g., internal hard disks or removable disks or magnetic tapes; magneto optical disks; and CD-ROM and DVD-ROM disks. The processor and the memory can be supplemented by, or incorporated in, special purpose logic circuitry. The components of the system can be interconnected by any form or medium of digital data communication, e.g., a communication network. Examples of communication networks include a local area network ("LAN") and a wide area network ("WAN"), e.g., the Internet.

Those skilled in the art should appreciate that such computer instructions can be written in a number of programming languages for use with many computer architectures or operating systems. Furthermore, such instructions may be stored in any memory device, such as semiconductor, magnetic, optical or other memory devices, and may be transmitted using any communications technology, such as optical, infrared, microwave, or other transmission technologies.

Among other ways, such a computer program product may be distributed as a removable medium with accompanying printed or electronic documentation (e.g., shrink-wrapped software), preloaded with a computer system (e.g., on system ROM or fixed disk), or distributed from a server or electronic bulletin board over the network (e.g., the Internet or World Wide Web). In fact, some embodiments may be implemented in a software-as-a-service model ("SAAS") or cloud-computing model. Of course, some embodiments of the present disclosure may be implemented as a combination of both software (e.g., a computer program product) and hardware. Still other embodiments of the present disclosure are implemented as entirely hardware, or entirely software.

Examples of the above-described embodiments can include the following:

1. A wearable optical device comprising:
    a ring configured to surround an appendage, the ring comprising an outer surface and an inner surface facing the appendage;
    a plurality of light sources disposed circumferentially about the inner surface and configured to direct light towards the appendage;
    a plurality of detectors disposed circumferentially about the inner surface, each detector configured to receive light from the appendage, the light being reflected from and/or transmitted through the appendage from at least one of the plurality of light sources; and
    a circuit board disposed within the ring and operatively connected to each of the plurality of light sources and the plurality of detectors,
    wherein the plurality of light sources and the plurality of detectors are configured to operate together to generate data suitable for conducting diffuse optical tomography on the appendage.

2. The device of example 1, wherein the device defines an open position wherein the plurality of light sources and the plurality of detectors are disposed proximal to the inner surface and a closed position where the plurality of light sources and the plurality of detectors are contacting the appendage, the device being operable to move between the open position and the closed position.

3. The device of examples 1 to 2, wherein each of the plurality of light sources comprises a contact surface configured to contact the appendage and each of the plurality of detectors comprises a contact surface configured to contact the appendage, wherein the plurality of light sources and the plurality of detectors are arranged in pairs.

4. The device of examples 1 to 3, wherein each light source and detector of each pair is disposed within a common housing.

5. The device of examples 1 to 4, further comprising a carrier disposed within a recess formed in the inner surface of the ring, the carrier configured to couple the plurality of light sources and the plurality of detectors to the ring.

6. The device of examples 4 to 5, further comprising a plurality of biasing mechanisms each configured to bias a respective one of the common housings towards the appendage.

7. The device of examples 4 to 6, wherein each common housing is configured to move along a respective radial axis and is prevented from rotating relative to the carrier.
8. The device of examples 1 to 7, comprising a plurality of pressure sensors, each pressure sensor configured to measure pressure of the appendage against the contact surfaces of at least one of a respective one of the plurality of light sources and the plurality of detectors.
9. The device of examples 1 to 8, comprising a plurality of position sensors, each position sensor configured to measure radial deflection of at least one of the plurality of light sources and the plurality of detectors by the appendage.
10. The device of examples 1 to 9, wherein the plurality of light sources comprises eight light sources disposed at equal intervals about the circumference of the inner surface, and wherein the plurality of detectors comprises eight detectors disposed at equal intervals about the circumference of the inner surface.
11. The device of examples 1 to 10, wherein each light source of the plurality of light sources comprises an array of light-emitting diodes, each array comprising a plurality of individual light-emitting diodes each configured to emit light in a different wavelength.
12. The device of examples 1 to 11, comprising a microcontroller configured to cause the emission of light from each of the plurality of light sources and receive the data from each of the plurality of detectors.
13. The device of examples 1 to 12, comprising a wireless transmitter configured to transmit the data.
14. The device of examples 1 to 13, further at least one of: a skin temperature sensor, an ambient temperature sensor, or a sensor configured to measure movement of the device.
15. A method of obtaining a signal from a subject comprising:
given a wearable optical device disposed around an appendage, the device comprising a plurality of light sources and a plurality of detectors disposed circumferentially around the appendage;
emitting light from one of the plurality of light sources individually;
receiving signals from each of the plurality of detectors,
repeating the emitting and receiving for each of the plurality of light sources; and
generating data from the received signals, the data being suitable for conducting 2D or 3D diffuse optical tomography on the appendage.
16. The method of example 15, further comprising moving the plurality of light sources and the plurality of detectors towards the appendage until they contact the appendage.
17. The method of examples 15 to 16, wherein the signals are received from two or more photodiodes at a time.
18. The method of examples 15 to 17, further comprising:
receiving by a processor, the data from the device of disposed around the appendage;
reconstructing an image of the appendage using the data and diffuse optical tomography techniques;
isolating a biosignal from an internal structure within the appendage; and
providing physiological information based on the biosignal.
19. The method of example 18, wherein the biosignal comprises a dynamic signal and the physiological information comprises at least one of: blood volume changes, blood oxygenation, blood velocity, pulse wave velocity, or blood flow.
20. The method of examples 18 to 19, wherein the biosignal comprises a static signal and the physiological information comprises at least one of: bone location, tendon location, fat concentration, or water concentration.
21. The method of examples 18 to 20, wherein the image is reconstructed and the physiological information is provided in real-time.
22. The method of examples 18 to 21, wherein the internal structure is a main artery of the appendage.
23. The method of examples 18 to 22, wherein the data is processed using a deep learning model to obtain the reconstructed image of the appendage.

One skilled in the art will readily appreciate that the present disclosure is well adapted to carry out the objects and obtain the ends and advantages mentioned, as well as those inherent therein. The present disclosure described herein are presently representative of preferred embodiments, are exemplary, and are not intended as limitations on the scope of the present disclosure. Changes therein and other uses will occur to those skilled in the art which are encompassed within the spirit of the present disclosure as defined by the scope of the claims.

The invention claimed is:
1. A wearable optical device comprising:
a ring configured to surround an appendage, the ring comprising an outer surface and an inner surface facing the appendage;
a plurality of light sources disposed circumferentially about the inner surface and configured to direct light towards the appendage;
a plurality of detectors disposed circumferentially about the inner surface, each detector configured to receive light from the appendage, the light being reflected from and/or transmitted through the appendage from at least one of the plurality of light sources; and
a circuit board disposed within the ring and operatively connected to each of the plurality of light sources and each of the plurality of detectors,
wherein the plurality of light sources and the plurality of detectors are configured to operate together to generate data suitable for conducting diffuse optical tomography on the appendage,
wherein the ring includes a stationary section and a rotatable section rotatably coupled to the stationary section and configured to change the device between (i) an open configuration in which the plurality of light sources and the plurality of detectors move outwardly away from a centerpoint of the ring to be disposed proximal to the inner surface of the ring and (ii) a closed configuration in which the plurality of light sources and the plurality of detectors move inwardly toward the centerpoint of the ring to contact the appendage.
2. The device of claim 1, wherein each of the plurality of light sources comprises a contact surface configured to contact the appendage and each of the plurality of detectors comprises a contact surface configured to contact the appendage, wherein the plurality of light sources and the plurality of detectors are arranged in pairs.
3. The device of claim 2, wherein each light source and detector of each pair is disposed within a common housing.
4. The device of claim 3, further comprising a carrier disposed within a recess formed in the inner surface of the ring, the carrier configured to couple the plurality of light sources and the plurality of detectors to the ring.

5. The device of claim 3, further comprising a plurality of biasing mechanisms each configured to bias a respective one of the common housings towards the appendage.

6. The device of claim 3, wherein each common housing is configured to move along a respective radial axis and is prevented from rotating relative to the carrier.

7. The device of claim 2, further comprising a plurality of pressure sensors, each pressure sensor configured to measure pressure of the appendage against the contact surfaces of at least one of a respective one of the plurality of light sources and the plurality of detectors.

8. The device of claim 1, further comprising a plurality of position sensors, each position sensor configured to measure radial deflection of at least one of the plurality of light sources and the plurality of detectors by the appendage.

9. The device of claim 1, wherein the plurality of light sources comprises eight light sources disposed at equal intervals about the circumference of the inner surface, and wherein the plurality of detectors comprises eight detectors disposed at equal intervals about the circumference of the inner surface.

10. The device of claim 1, wherein each light source of the plurality of light sources comprises an array of light-emitting diodes, each array comprising a plurality of individual light-emitting diodes each configured to emit light in a different wavelength.

11. The device of claim 1, further comprising a microcontroller configured to cause the emission of light from each of the plurality of light sources and receive the data from each of the plurality of detectors.

12. The device of claim 1, further comprising a wireless transmitter configured to transmit the data.

13. The device of claim 1, further comprising at least one of: a skin temperature sensor, an ambient temperature sensor, or a sensor configured to measure movement of the device.

14. A method of obtaining a signal from a subject comprising:
given a wearable optical device disposed around an appendage, the device comprising a plurality of light sources and a plurality of detectors disposed circumferentially around the appendage;
rotating a rotatable section of the device relative to a stationary section of the device to cause the plurality of light sources and the plurality of detectors to move inwardly toward a centerpoint of the device;
emitting light from one of the plurality of light sources individually;
receiving signals from each of the plurality of detectors, repeating the emitting and receiving for each of the plurality of light sources; and
generating data from the received signals, the data being suitable for conducting 2D or 3D diffuse optical tomography on the appendage.

15. The method of claim 14, wherein the step of rotating includes moving the plurality of light sources and the plurality of detectors towards the appendage until they contact the appendage.

16. The method of claim 14, wherein the signals are received from two or more of the plurality of detectors at a time.

17. The method of claim 14, further comprising:
receiving by a processor, the data from the device disposed around the appendage;
reconstructing an image of the appendage using the data and diffuse optical tomography techniques;
isolating a biosignal from an internal structure within the appendage; and
providing physiological information based on the biosignal.

18. The method of claim 17, wherein the biosignal comprises a dynamic signal and the physiological information comprises at least one of: blood volume changes, blood oxygenation, blood velocity, pulse wave velocity, or blood flow.

19. The method of claim 17, wherein the biosignal comprises a static signal and the physiological information comprises at least one of: bone location, tendon location, fat concentration, or water concentration.

20. The method of claim 17, wherein the image is reconstructed and the physiological information is provided in real-time.

21. The method of claim 17, wherein the internal structure is a main artery of the appendage.

22. The method of claim 17, wherein the data is processed using a deep learning model to obtain the reconstructed image of the appendage.

* * * * *